(12) United States Patent
McFadden et al.

(10) Patent No.: US 12,398,375 B2
(45) Date of Patent: Aug. 26, 2025

(54) METHODS FOR IMPROVED POXVIRUS YIELDS

(71) Applicant: ARIZONA BOARD OF REGENTS ON BEHALF OF ARIZONA STATE UNIVERSITY, Scottsdale, AZ (US)

(72) Inventors: Douglas Grant McFadden, Tempe, AZ (US); Mohammed Masmudur Rahman, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 996 days.

(21) Appl. No.: 17/266,499

(22) PCT Filed: Aug. 7, 2019

(86) PCT No.: PCT/US2019/045452
§ 371 (c)(1),
(2) Date: Feb. 5, 2021

(87) PCT Pub. No.: WO2020/033510
PCT Pub. Date: Feb. 13, 2020

(65) Prior Publication Data

US 2021/0301263 A1 Sep. 30, 2021

Related U.S. Application Data

(60) Provisional application No. 62/716,224, filed on Aug. 8, 2018.

(51) Int. Cl.
*C12N 7/00* (2006.01)
*A61P 31/00* (2006.01)

(52) U.S. Cl.
CPC ................ *C12N 7/00* (2013.01); *A61P 31/00* (2018.01); *C12N 2710/24051* (2013.01); *C12N 2710/24151* (2013.01)

(58) Field of Classification Search
CPC ............ C12N 7/00; C12N 2710/24051; C12N 2710/24151; A61P 31/00
See application file for complete search history.

(56) References Cited

U.S. PATENT DOCUMENTS

| | | | |
|---|---|---|---|
| 10,238,700 | B2 | 3/2019 | Szalay et al. |
| 2004/0014034 | A1 | 1/2004 | Evans et al. |
| 2009/0035276 | A1 | 2/2009 | McFadden et al. |
| 2012/0100109 | A1 | 4/2012 | Zhang et al. |
| 2014/0134134 | A1 | 5/2014 | McFadden et al. |
| 2022/0296660 | A1 | 9/2022 | McFadden et al. |

FOREIGN PATENT DOCUMENTS

| | | | |
|---|---|---|---|
| WO | WO-2004015118 | A1 | 2/2004 |
| WO | WO-2004022729 | A1 | 3/2004 |
| WO | WO-2020033510 | A1 | 2/2020 |
| WO | WO-2021046048 | A1 | 3/2021 |

OTHER PUBLICATIONS

Hou J. (Interactions of Vaccinia virus with the host cell. Thesis, 2016, The University of Edinburgh; https://www.era.lib.ed.ac.uk/handle/1842/22898?show=full (pub. 2017). (Year: 2017).*

Fenner F. Adventures with poxviruses of vertebrates. FEMS Microbiol Rev. Apr. 2000;24(2): 123-33. (Year: 2000).*

Chan WM, McFadden G. Oncolytic Poxviruses. Annu Rev Virol. Sep. 1, 2014;1(1):119-141. (Year: 2014).*

Slezak K, Michalik M, Kowalczyk A, Rokita H. YY1 is recruited to the cytoplasm of vaccinia virus-infected human macrophages by the Crm1 system. Virus Res. Jun. 15, 2004;102(2):177-84. (Year: 2004).*

Lundberg et al. Selective Inhibitor of Nuclear Export (SINE) Compounds Alter New World Alphavirus Capsid Localization and Reduce Viral Replication in Mammalian Cells. PLoS Negl Trop Dis. Nov. 30, 2016;10(11):e0005122. (Year: 2016).*

EP Application No. 19846898.5 Extended European Search Report dated Apr. 11, 2022.

Fahy et al.: Vaccinia virus protein C16 acts intracellularly to modulate the host response and promote virulence. J Gen Virol. 89(Pt 10):2377-2387 doi:10.1099/vir.0.2008/004895-0 (2008).

Lundberg et al.: Selective Inhibitor of Nuclear Export (SINE) Compounds Alter New World Alphavirus Capsid Localization and Reduce Viral Replication in Mammalian Cells. PLoS Negl Trop Dis. 10(11):e0005122:1-24 doi:10.1371/journal.pntd.0005122 (2016).

Sun et al.: Inhibiting cancer cell hallmark features through nuclear export inhibition. Signal Transduct Target Ther. 1:16010:1-10 doi:10.1038/sigtrans.2016.10 (2016).

Bachmann et al., A nuclear transport signal in mammalian target of rapamycin is critical for its cytoplasmic signaling to S6 kinase 1. J Biol Chem 281(11):7357-7363 (2006).

Cameron et al. The complete DNA sequence of Myxoma Virus. Virology 264:298-318 (1999).

Chan et al., Oncolytic Myxoma Virus: The path to clinic. Vaccine 31(39):4252-4258 (2013).

Chan et al., Oncolytic Poxviruses. Annu Rev Virol 1(1):119-141 (2014).

Chan et al. Oncolytic poxviruses. Annual review of virology 1:191-214 (2014).

Dickmanns et al. Structural Basis of Targeting the Exportin CRM1 in Cancer. Cells 4(3):538-68 (2015).

Hou, J. Interactions of Vaccinia virus with the host cell. [2016 Thesis] The University of Edinburgh; https://www.era.lib.ed.ac.uk/handle/1842/22898?show=full (pub. 2017).

(Continued)

*Primary Examiner* — Janet L Andres
*Assistant Examiner* — Ruixue Wang
(74) *Attorney, Agent, or Firm* — Riverside Law LLP

(57) ABSTRACT

A method of producing poxviruses at an increased growth rate and/or progeny virus titer in cells, the method including: contacting a host cell with an effective amount of nucleo-cytoplasmic transport inhibitor; contacting the host cell with a poxvirus of interest under conditions that permit the poxvirus of interest to adsorb to the surface of the host cell; and culturing the host cell to produce progeny poxvirus of interest.

12 Claims, 8 Drawing Sheets

(56) References Cited**

OTHER PUBLICATIONS

Kalesse et al. The chemistry and biology of ratjadone. Chembiochem. 2(9):709-14 (2001).
Koster et al. Ratjadones inhibit nuclear export by blocking CRM1/exportin 1. Exp Cell Res, 286(2):321-31 (2003).
Kudo et al. Leptomycin B inhibition of signal-mediated nuclear export by direct binding to CRAII. Exp Cell Res 242(2):540-7 (1998).
Lichty et al. Going viral with cancer immunotherapy. Nature Reviews Cancer 14:559-567 (2014).
Matthew et al. CRM1 inhibitors for antiviral therapy. Frontiers in Microbiology 8:1171 (2017).
McFadden. Poxvirus tropism. Nat Rev Microbiol 3(3):201-13 (2005).
Moss. Chapter 84: Poxviridae: The Viruses and Their Replication. Fields' virology B. N. Fields, D. M. Knipe, P. M. Howley, D. E. Griffin, Eds. (Lippincott Williams & Wilkins, Philadelphia (pp. 2849-2883) (2001).
Mutka et al. Identification of nuclear export inhibitors with potent anticancer activity in vivo. Cancer Res. 69(2):510-7 (2009).
Oh et al., Host cell nuclear proteins are recruited to cytoplasmic vaccinia virus replication complexes. Journal of Virology 79(20):12852-12860 (2005).
PCT/US2019/045452 International Search Report and Written Opinion dated Nov. 8, 2019.
PCT/US2020/048932 International Search Report and Written Opinion dated Dec. 9, 2020.
Pemberton et al. Paschal, Mechanisms of receptor-mediated nuclear import and nuclear export. Traffic 6(3):187-98 (2005).
Postigo et al. Cytoplasmic ATR Activation Promotes Vaccinia Virus Genome Replication. Cell Rep 19(5):1022-1032 (2017).
Rahman et al. Identification of host DEAD-box RNA helicases that regulate cellular tropism of oncolytic Myxoma virus in human cancer cells. Sci Rep 7(1):15710 (2017).
Realegeno et al. Monkeypox Virus Host Factor Screen Using Haploid Cells Identifies Essential Role of GARP Complex in Extracellular Virus Formation. J Virol 91(11):e00011-17 (2017).
Seet et al. Poxviruses and immune evasion. Annu Rev Immunol 21:377-423 (2003).
Smith et al. Vaccinia virus immune evasion: mechanisms, virulence and immunogenicity. J Gen Virol 94(Pt 11):2367-92 (2013).
Turner et al. Nuclear export of proteins and drug resistance in cancer. Biochem Pharmacol 83(8):1021-32 (2012).
Upton et al. Poxvirus orthologous clusters: toward defining the minimum essential poxvirus genome. J Virol 77(13):7590-600 (2003).
Adam et al. Synergistic and Selective Cancer Cell Killing Mediated by the Oncolytic Adenoviral Mutant AdΔΔ and Dietary Phytochemicals in Prostate Cancer Models. Hum Gene Ther 23(9):1003-1015 (2012).
Fehl et al. Curcumin promotes the oncoltyic capacity of vesicular stomatitis virus for the treatment of prostate cancers. Virus Res 228:14-23 (2017).
Riaz et al. Selinexor. Exportin-1 (XPO1) inhibitor, Oncolytic. Drugs of the Future 39(10):685 (2014).
Zemp et al. Treating brain tumor-initiating cells using a combination of myxoma virus and rapamycin. Neuro Oncol 15(7):904-920 (2013).

\* cited by examiner

METHODS FOR IMPROVED POXVIRUS YIELDS

CROSS-REFERENCE

This application is a national phase entry of International Application No. PCT/US2019/045452, filed Aug. 7, 2019, which claims priority to U.S. Provisional Patent Application No. 62/716,224 filed Aug. 8, 2018, each of which is incorporated herein by reference in its entirety.

STATEMENT OF GOVERNMENT SUPPORT

This invention was made with government support under grant number RO1 AI080607 awarded by the National Institutes of Health. The government has certain rights in the invention.

TECHNICAL FIELD

This disclosure relates to poxvirus and, in particular, to methods of producing poxvirus at a high yield in vitro.

BACKGROUND

Oncolytic viruses, such as from the Poxviridae family of viruses, are mammalian viruses that are designed and/or selected for their ability to selectively infect and kill transformed cancer cells, and by their ability to activate host's immune system against not only the virus, but also tumor antigens (see for example, Lichty B D, Breitbach C J, Stojdl D F, Bell J C. 2014. *Going viral with cancer immunotherapy*. Nature Reviews Cancer 14:559-567). Members of Poxviridae family of viruses are a diverse group of large, complex double-stranded DNA viruses that can replicate in the cytoplasm of infected cells. The genomes of most poxviruses are about 150,000 to 300,000 base pairs in length and encode approximately 150 to 300 proteins. About half of these viral proteins are highly conserved between different poxvirus members and perform essential functions like cell binding and entry, genome replication, transcription and virion assembly (Upton, C., et al., *Poxvirus orthologous clusters: toward defining the minimum essential poxvirus genome*. J Virol, 2003. 77(13): p. 7590-600). Other viral proteins are involved in evading many host defense functions (Smith, G. L., et al., *Vaccinia virus immune evasion: mechanisms, virulence and immunogenicity*. J Gen Virol, 2013. 94(Pt 11): p. 2367-92). The poxviral genes can be expressed in distinct phases. For example, the early gene products can include proteins that are necessary for viral DNA replication and are expressed before the DNA is replicated. On the other hand, the intermediate/late gene products expressed during or after DNA replication can include the structural proteins required for virion maturation. All the steps of this complex viral replication process (starting from un-coating the genome, early gene expression, DNA replication, late gene expression and an even more complex virion maturation processes) can occur exclusively in the cytoplasm of the infected cells.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Disclosed herein, in some aspects, is a method for replicating a poxvirus, comprising: exposing a host cell to an effective amount of a nucleocytoplasmic transport inhibitor and the poxvirus under conditions that permit the poxvirus to adsorb to the surface of the host cell; and incubating the infected host cell in a culture medium to allow for replication of the poxvirus.

In some embodiments, the method further comprising harvesting the poxvirus produced in the host cell. In some embodiments, the poxvirus is genetically modified. In some embodiments, the poxvirus is a Leporipoxvirus. In some embodiments, the Leporipoxvirus is a myxoma virus. In some embodiments, the poxvirus is an Orthopoxvirus. In some embodiments, the Orthopoxvirus is a vaccinia virus. In some embodiments, the vaccinia virus is a vaccinia virus strain selected from the group consisting of Lister, Wyeth, Western Reserve, Modified Vaccinia virus Ankara, and LC16m series. In some embodiments, the Orthopoxvirus is a Raccoonpox virus. In some embodiments, the poxvirus is a Capripox virus. In some embodiments, the Capripox virus is an Orf virus. In some embodiments, the nucleocytoplasmic transport inhibitor is selected from the group consisting of Leptomycin A, Leptomycin B, Ratjadone A, Ratjadone B, Ratjadone C, Ratjadone D, Anguinomycin A, Goniothalamin, piperlongumine, plumbagin, curcumin, valtrate, acetoxychavicol acetate, prenylcoumarin osthol, KOS 2464, PKF050-638, CBS9106, and Selinexor. In some embodiments, the method further comprises contacting the host cell with the nucleocytoplasmic transport inhibitor prior to infecting the host cell with the poxvirus. In some embodiments, the method further comprises contacting the host cell with the nucleocytoplasmic transport inhibitor after infecting the host cell with the poxvirus. In some embodiments, the method further comprises exposing the host cell to the nucleocytoplasmic transport inhibitor and the poxvirus at the same time. In some embodiments, the poxvirus is replicated at a rate that is at least 30% faster than a replication rate in an absence of the nucleocytoplasmic transport inhibitor. In some embodiments, the nucleocytoplasmic transport inhibitor increases the replication of the poxvirus by at least 3 fold after 24 hours post infection. In some embodiments, the host cell is contacted with the poxvirus at a multiplicity of infection (MOI) lower than 2.0. In some embodiments, the effective amount of the nucleocytoplasmic transport inhibitor is in the range of about 0.0005 µM to about 0.5 µM. In some embodiments, the culture medium comprises the nucleocytoplasmic transport inhibitor. In some embodiments, the host cell is an immortalized human or primate cell. In some embodiments, the host cell is from a cell line used in good manufacturing practices (GMP) for manufacture of the poxvirus. In some embodiments, the host cell is a Human A549 cell, a HeLa cell, a 239 cell, or a primate Vero cell. In some embodiments, the method further comprises removing un-adsorbed poxvirus.

Disclosed herein, in some aspects, is a method of producing poxviruses at an increased growth rate and/or titer in cells, the method comprising: contacting a host cell with an effective amount of a nucleocytoplasmic transport inhibitor; contacting the host cell with a poxvirus of interest under conditions that permit the poxvirus of interest to adsorb to a surface of the host cell; and culturing the host cell to produce progeny of the poxvirus of interest.

In some embodiments, the method further comprises harvesting the progeny of the poxvirus of interest. In some embodiments, the poxvirus of interest is genetically modified. In some embodiments, the nucleocytoplasmic transport inhibitor comprises one or more of Leptomycin A, Leptomycin B, Ratjadone A, Ratjadone B, Ratjadone C, Ratjadone D, Anguinomycin A, Goniothalamin, piperlongumine, plumbagin, curcumin, valtrate, acetoxychavicol acetate, prenylcoumarin osthol, KOS 2464, PKF050-638, CBS9106, or Selinexor. In some embodiments, the host cell is cultured in a presence of an effective amount of the nucleocytoplasmic transport inhibitor. In some embodiments, the poxvirus of interest is an oncolytic virus candidate. In some embodiments, the poxvirus of interest is a Leporipoxvirus. In some embodiments, the Leporipoxvirus is a myxoma virus. In some embodiments, the poxvirus of interest is an Orthopoxvirus. In some embodiments, the Orthopoxvirus is a vaccinia virus. In some embodiments, the vaccinia virus is a vaccinia virus strain selected from the group consisting of Lister, Wyeth, Western Reserve, Modified Vaccinia virus Ankara, and LC16m series. In some embodiments, the Orthopoxvirus is a Raccoonpox virus. In some embodiments, the poxvirus of interest is a Capripox virus. In some embodiments, the Capripox virus is an Orf virus. In some embodiments, the host cell is an immortalized human or primate cell. In some embodiments, the host cell is from a cell line used in good manufacturing practices (GMP) for manufacture of the poxvirus of interest. In some embodiments, the host cell is a Human A549 cell, a HeLa cell, a 239 cell, or a primate Vero cell. In some embodiments, the host cell is contacted with the poxvirus of interest at a multiplicity of infection (MOI) of between about 0.01 and 1.0. In some embodiments, the method further comprises removing un-adsorbed poxvirus of interest prior to the culturing. In some embodiments, the effective amount of the nucleocytoplasmic transport inhibitor is between about 0.0005 µM and about 0.5 µM.

BRIEF DESCRIPTION OF THE DRAWINGS

FIGS. 5A-5D are a set of bar graphs showing that nucleocytoplasmic transport inhibitors enhanced MYXV replication in human A549 cells, resulting in higher levels of progeny virus. A549 cells were pre-treated with nucleocytoplasmic transport inhibitors Leptomycin A (FIG. 5A), Leptomycin B (FIG. 5B), Ratjadone A (FIG. 5C) or Anguinomycin A (FIG. 5D) for 1 h. The cells were then infected with vMyx-GFP at an MOI of 1.0, 0.1 or 0.01 for 1 h. After 1 h the un-adsorbed viruses were removed, washed, and incubated with media in the presence of the respective inhibitors. The infected cells were harvested after 48 h and virus titers were determined following serial dilutions onto RK13 cells. The concentrations of inhibitors are indicated by the numbers above the bars. 1 denotes no inhibitor, 2 denotes 0.01 µM (10 nM) of inhibitor. 3 denotes 0.001 µM (1 nM) of inhibitor, 4 denotes 0.1 µM (100 nM) of inhibitor.

FIGS. 6A and 6B are a set of bar graphs showing that nucleocytoplasmic transport inhibitors enhanced MYXV replication in human A549 cells, resulting in higher levels of progeny virus. A549 cells were mock-treated, or pre-treated with nucleocytoplasmic transport inhibitors for 1 h. The treatments are indicated by the numbers above the bars of the graph; 1 indicates mock treatment, 2 indicates Leptomycin A, 3 indicates Leptomycin B, 4 indicates Ratjadone A, and 5 indicates Anguinomycin A. The cells were then infected with vMyx-GFP at an MOI of 0.1 or 0.01 for 1 h. After 1 h the un-adsorbed viruses were removed, and cells were washed and incubated with media in the presence of the respective inhibitors. The infected cells were harvested after 48 h (FIG. 6A) or 72 h (FIG. 6B) and virus titers were determined following serial dilutions onto RK13 cells.

DETAILED DESCRIPTION

The present disclosure provides methods of increasing oncolytic virus such as poxvirus production yields in transformed human and primate cells, for example, those commonly used for GMP manufacture. Oncolytic virus candidates, such as myxoma virus (MYXV) and vaccinia virus (VACV) of the poxviruses group, present some unique challenges in large-scale manufacture and purification. Due to its large size, poxviruses cannot be sterilized by filtration and thus any manufacturing process is typically closed, and the purification often requires the lysis of the infected cell and the purification of the viral particles from the cellular debris. The present disclosure involve the surprising finding that treating host cell lines with agents, such as one or more nucleocytoplasmic transport inhibitors can increase the replication and ultimate yields of overall infectious poxvirus. The disclosed method thus provides a highly efficient way to increase the overall yield of poxviruses, such as MYXV and VACV, in host cells such as transformed human and primate cells used for virus GMP manufacture.

Unless otherwise noted, technical terms are used according to conventional usage. Definitions of common terms in molecular biology can be found in Benjamin Lewin, Genes VII, published by Oxford University Press, 1999; Kendrew et al. (eds.), The Encyclopedia of Molecular Biology, published by Blackwell Science Ltd., 1994; and Robert A. Meyers (ed.), Molecular Biology and Biotechnology: a Comprehensive Desk Reference, published by VCH Publishers, Inc., 1995; and other similar references.

Unless otherwise explained, all technical and scientific terms used herein have the same meaning as commonly understood by one of ordinary skill in the art to which this disclosure belongs. Although methods and materials similar or equivalent to those described herein can be used in the practice or testing of this disclosure, suitable methods and materials are described below. In addition, the materials, methods, and examples are illustrative only and not intended to be limiting.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular forms "a," "an," and "the" are intended to include the plural forms as well, unless the context clearly indicates otherwise.

As used herein, the term "and/or" refers to and encompasses any and all possible combinations of one or more of the associated listed items, as well as the lack of combinations when interpreted in the alternative ("or").

As used herein, "one or more" or at least one can mean one, two, three, four, five, six, seven, eight, nine, ten or more, up to any number.

As used herein, the term "comprises" or "comprising" means "includes." Hence "comprising A or B" means including A, B, or A and B. "Comprise" and variations of the term, such as "comprising", "comprises" and "comprised", as used herein, is meant that various additional components or steps can be conjointly employed.

An "effective amount" refers to an amount of a compound or composition that is sufficient to produce a desired effect, for example an increase in the production of a poxvirus. In this example, the effective amount will vary with type of the cell and the particular agent administered, the duration of the treatment, the nature of any concurrent treatment, and like factors within the knowledge and expertise of those skilled in the art.

The term "a host cell" or a "cell" as used herein includes a single cell as well as a plurality or population of cells (e.g., a eukaryotic cell or a population of eukaryotic cells) in various species, including human. The term also includes any progeny of the subject host cell. All progeny of the host cell may not be identical to the parental cell since there may be mutations that occur during replication. However, such progeny are included when the term "host cell" is used. Contacting or exposing an agent to a cell includes placing the agent in the growth media of the cell.

A "nucleocytoplasmic transport inhibitor" is an agent that inhibits transport of molecules through the nuclear export pathway. Examples of nucleocytoplasmic transport inhibitor include but are not limited to Leptomycin A, Leptomycin B, Ratjadone A, Ratjadone B, Ratjadone C, Ratjadone D, Anguinomycin A, Goniothalamin, piperlongumine, plumbagin, curcumin, valtrate, acetoxychavicol acetate, prenylcoumarin osthol, KOS 2464, PKF050-638, CBS9106, and Selinexor.

A "virus" is a microscopic infectious organism that reproduces inside living cells. A virus can consist essentially of a core of a single nucleic acid surrounded by a protein coat, and has the ability to replicate only inside a living cell. "Viral replication" is the production of additional virus by the occurrence of at least one viral life cycle. A virus may subvert the host cell's normal functions, causing the cell to behave in a manner determined by the virus. For example, a viral infection may result in a cell producing a cytokine, or responding to a cytokine, when the uninfected cell does not normally do so. The term "replication-competent" as used herein refers to a virus that is capable of infecting and replicating within a particular host cell.

A "poxvirus" is a virus from the Poxviridae family. Poxviruses are double-stranded DNA viruses that are capable of infecting both vertebrates and invertebrates. Poxviruses include, for example, species and genera of viruses that are classified as being a part of the Chordopoxvirinae subfamily such as Orthopoxvirus, Parapoxvirus, Avipoxvirus, Capripoxvirus, Leporipoxvirus, Suipoxvirus, Molluscipoxvirus, and Yatapoxvirus genera, and the Entomopoxvirinae subfamily, including Alphaentomopoxvirus, Betaentomopoxvirus, and Gammaentomopoxvirus genera.

"Contacting" means placement in direct physical association. Contacting includes contact between a molecule, such as an inhibitor and a cell, for example by placing an agent in direct physical association with a cell, such as in culture with a cell.

"Inhibit" means to reduce to a measurable extent. For example to reduce transport in the nuclear export pathway. An "inhibitor" is a substance capable of inhibiting to some measurable extent, for example, transport in the nuclear export pathway.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods fom*

*Current Protocols in Molecular Biology,* 4th ed., Wiley & Sons, 1999; Harlow and Lane, *Antibodies: A Laboratory Manual,* Cold Spring Harbor Laboratory Press, 1990; and Harlow and Lane, *Using Antibodies: A Laboratory Manual,* Cold Spring Harbor Laboratory Press, 1999. In addition, the materials, methods, and examples are illustrative only and not intended to be limiting.

Poxviruses are large DNA viruses which can replicate exclusively within the cytoplasm of the infected cells. They can encode all of the proteins required for DNA and mRNA synthesis. Apart from viral proteins involved in poxvirus replication, about half of the poxvirus genome encode proteins that have been shown to be required for the inhibition or manipulation of diverse intracellular anti-viral signaling pathways functioning in the cytoplasm and nucleus. However, there is evidence that host cell proteins from cytoplasm and nuclear compartments participate in at least some steps of poxvirus replication. However, in this context, the role of cellular nuclear proteins that shuttle between cytoplasmic and nuclear compartments during poxvirus infection and replication is not well understood. The role of host cell proteins during this entire replication cycle has been documented in some steps, for example, nuclear proteins ATR, RPA, INTS7 and Chkl are recruited from the cell nucleus to the viral factories for optimal virus genome replication (Postigo, A., et al., *Cytoplasmic ATR Activation Promotes Vaccinia Virus Genome Replication. Cell Rep,* 2017. 19(5): p. 1022-1032). In another study, it was shown that the Golgi-associated retrograde protein (GARP) complex is required for extracellular virus (EV) formation of Vaccinia virus (VACV) (Realegeno, S., et al., *Monkeypox Virus Host Factor Screen Using Haploid Cells Identifies Essential Role of GARP Complex in Extracellular Virus Formation.* J Virol, 2017. 91(11)). Nuclear transcription factors YY1, Spl and TATA binding protein were found to co-localize with VACV replication complexes (Oh, J. and S. S. Broyles, *Host cell nuclear proteins are recruited to cytoplasmic vaccinia virus replication complexes.* J Virol, 2005. 79(20): p. 12852-60).

Many diverse cellular proteins and signaling pathways have been implicated in defending the cell against the infection and replication of poxviruses. This is why more than half of the genome-encoded poxvirus proteins are involved in the specific inhibition or modulation of these host anti-viral pathways (Smith, G. L., et al., *Vaccinia virus immune evasion: mechanisms, virulence and immunogenicity.* J Gen Virol, 2013. 94(Pt 11): p. 2367-92; Seet, B. T., et al., *Poxviruses and immune evasion.* Annu Rev Immunol, 2003. 21: p. 377-423). In some cases, the virus-encoded proteins function in a host specific manner and determine whether a given poxvirus will be able to successfully infect and replicate in a specific species of host (McFadden, G., *Poxvirus tropism.* Nat Rev Microbiol, 2005. 3(3): p. 201-13). Members of poxviruses, for example, Myxoma virus (MYXV), a Leporipoxvirus, and vaccinia virus (VACV), an orthopoxvirus, could be developed as oncolytic viruses for the treatment of human cancers (Chan, W. M. and G. McFadden, *Oncolytic Poxviruses.* Annu Rev Virol, 2014. 1(1): p. 119-141). In this context, it is important to understand how poxvirus-encoded proteins counteract the immune system in a host that is different to their natural host. For example, it is important to understand the role of host cell nuclear proteins that shuttle between the nuclear and cytoplasmic compartments during viral replication processes.

It was unexpectedly discovered that many drugs that inhibit the nuclear import/export pathway class can increase poxvirus yield in human cells commonly used for the GMP manufacture of these viruses.

MYXV is a rabbit-specific pathogen that is being developed as an oncolytic immunotherapeutic for the treatment of human cancers. The MYXV may be any virus that belongs to the Leporipoxvirus species of poxviruses that is replication-competent. The MYXV may be a wild-type strain of MYXV or it may be a genetically modified strain of MYXV. In some instances, the MYXV is Lausanne strain. In some instances, the MYXV is a South American MYXV strain that circulates in *Sylvilagus brasiliensis.* In some instances, the MYXV is a Californian MYXV strain that circulates in *Sylvilagus bachmani.* In some instances, the MYXV is 6918, an attenuated Spanish field strain that comprises modifications in genes M009L, M036L, M135R, and M148R (GenBank Accession number EU552530 which is hereby incorporated by reference as provided by GenBank on Jul. 27, 2019). In some instances, the MYXV is 6918VP60-T2 (GenBank Accession Number EU552531 which is hereby incorporated by reference as provided by GenBank on Jul. 27, 2019). In some instances, the MYXV is a strain termed the Standard laboratory Strain (SLS).

In some instances, the MYXV comprises at least 90%, 95%, 96%, 97%, 98%, or 99%, such as between 95% and 98%, 95% and 99%, including 90%, 91%, 92%, 93%, 94%, 95%, 96%, 97%, 98%, 99% sequence identity to a sequence disclosed in Cameron, et al., "The complete DNA sequence of Myxoma Virus," Virology 264: 298-318 (1999) (which is herein incorporated by reference in its entirety). In some cases, the MYXV comprises the sequence disclosed in Cameron, et al., "The complete DNA sequence of Myxoma Virus," Virology 264: 298-318 (1999).

In some embodiments, MYXV is non-pathogenic in humans but able to infect and kill a wide range of human cancer cells derived from different tissues. In normal primary human cells, the replication of MYXV can be restricted by multiple factors such as, for example, the cellular binding determinants, the intracellular anti-viral signaling pathways and type I IFN and/or other cytokines mediated cellular anti-viral states. In human cancer cells, these self-defense cell pathways are commonly defective. MYXV replication in some human cancer cells can depend on cellular RNA helicase family proteins (Rahman, M. M., et al., *Identification of host DEAD-box RNA helicases that regulate cellular tropism of oncolytic Myxoma virus in human cancer cells.* Sci Rep, 2017. 7(1): p. 15710). Without wishing to be bound by theory, RNA helicases which shuttle between nuclear and cytoplasmic compartments of cells may influence MYXV replication in virus-infected cells. Beside RNA helicases, other nuclear proteins may contribute to the replication cycle of MYXV and other poxviruses. For example, nuclear proteins might affect the replication efficiency of poxviruses in transformed human host cell lines.

Disclosed herein, in some embodiments, are methods for increasing or enhancing poxvirus gene expression and progeny virus formation using drug inhibitors of the nucleocytoplastic transport pathway. In some embodiments, inhibition of the nuclear export pathway in immortalized human cells commonly used for the GMP manufacture of poxviruses can be used to increase the viral yield from these cells. Thus, the disclosure provides a robust method of manufacturing potentially therapeutic poxvirus.

In some embodiments, this enhanced virus replication is most potent when cells are treated with an effective amount of inhibitor, for example, beginning just prior to the time of first virus adsorption. In some embodiments, an effective amount of inhibitor is determined for a given cell culture system (e.g., a given inhibitor, virus strain and host cell line). An effective amount of inhibitor can be determined, for example, by titrating the amount of the inhibitor in the cell culture system, and quantifying the yield of viral progeny as disclosed herein. In some embodiments, an effective amount of inhibitor can minimize drug-specific cellular toxicity, while increasing the yield of viral progeny. In some embodiments, an effective amount of a nucleocytoplasmic transport inhibitor is about 0.000001 µM to about 1 µM, about 0.000001 µM to about 0.1 µM, about 0.00001 µM to about 0.1 µM, about 0.00005 µM to about 0.05 µM, or about 0.00005 µM to about 0.005 µM. In some embodiments, an effective amount of a nucleocytoplasmic transport inhibitor is greater than about 0.000001 µM, about 0.000005 µM, about 0.00001 µM, about 0.00005 µM, about 0.0001, about 0.0005 µM, about 0.001 µM, about 0.005 µM, about 0.01 µM, about 0.05 µM, or about 0.1 µM. In some embodiments, an effective amount of a nucleocytoplasmic transport inhibitor is no more than about 0.0005 µM, about 0.001 µM, about 0.0015 µM, about 0.002 µM, about 0.0025 µM, about 0.003 µM, about 0.0035 µM, about 0.004 µM, about 0.0045 µM, about 0.005 µM, about 0.01 µM, about 0.015 µM, about 0.02 µM, about 0.025 µM, about 0.03 µM, about 0.035 µM, about 0.04 µM, about 0.045 µM, about 0.05 µM, about 0.1 µM, about 0.2 µM, about 0.25 µM, about 0.3 µM, about 0.4 µM, about 0.5 µM, about 0.75 µM, about 0.9 µM, about 1 µM, about 1.25 µM, about 1.5 µM, about 1.75 µM, about 2 µM, about 3 µM, about 4 µM, about 5 µM, about 6 µM, about 7 µM, about 8 µM, about 9 µM, or about 10 µM.

In some embodiments, enhanced virus replication occurs when the cells are infected at an effective multiplicity of infection (MOI) and then, for example, maintained in the continuous presence of the nucleocytoplasmic transport inhibitor. The MOI can be determined for a given cell culture system (e.g., a given inhibitor, virus strain and host cell line), for example, by titrating the ratio or virus to host cells in the cell culture system, and quantifying the yield of viral progeny as disclosed herein. In some embodiments, an effective MOI can minimize drug-specific cellular toxicity, while enhancing replication of the virus and increasing the yield of viral progeny.

The host cells can be contacted with a poxvirus of interest under conditions that permit the poxvirus of interest to adsorb to the surface of the host cells. In certain embodiments, the cells are contacted with the poxvirus of interest at a multiplicity of infection (MOI) of between about 0.001 to 2.0 or about 0.01 and 1.0, such as about 0.001 MOI, about 0.005 MOI, 0.01 MOI, about 0.02 MOI, about 0.03 MOI, about 0.04 MOI, about 0.05 MOI, about 0.06 MOI, about 0.07 MOI, about 0.08 MOI, about 0.09 MOI, about 0.1 MOI, about 0.15 MOI, about 0.2 MOI, about 0.25 MOI, about 0.3 MOI, about 0.35 MOI, about 0.4 MOI, about 0.45 MOI, about 0.5 MOI, about 0.55 MOI, about 0.6 MOI, about 0.65 MOI, about 0.7 MOI, about 0.75 MOI, about 0.8 MOI, about 0.85 MOI, about 0.9 MOI, about 0.95 MOI, about 1.0 MOI, about 1.1 MOI, about 1.2 MOI, about 1.3 MOI, about 1.4 MOI, about 1.5 MOI, about 1.6 MOI, about 1.7 MOI, about 1.8 MOI, about 1.9 MOI, or about 2.0 MOI. In some embodiments, the un-adsorbed poxvirus of interest is removed prior to culturing cells, for example by washing the cells. After treatment with the nucleocytoplasmic transport inhibitor, the host cells are cultured in the presence of the drug to produce progeny of the poxvirus of interest. Appropriate culture conditions can be selected based on the specific cell type. In some embodiments, the cells are allowed to incubate with the poxvirus of interest for a period of time to allow the poxvirus of interest to adsorb to the surface of the host cells, such as about 20 minutes to about 5 hours, for example about 20 minutes, about 25 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 2 hours, about 2.5 hours, about 3 hours, about 3.5 hours, about 4 hours, about 4.5 hours, about 5 hours, 12 hours, 18 hours, 20 hours, 24 hours, 30 hours, 36 hours, or even longer. In certain embodiments, the host cells are cultured in the presence of an effective amount of nucleocytoplasmic transport inhibitor, for example at the concentrations described above. The host cells can be cultured from about one to several days, such as 3 to 5 days before the progeny virus is harvested. In some embodiments, the method includes harvesting the progeny of the poxvirus of interest.

As disclosed herein, nucleocytoplasmic transport inhibitors can enhance virus replication and progeny virus yield in such cells. This drug-augmentation method provides a practical method to increase the yield of poxviruses, such as MYXV and VACV, which can be exploited for the large scale GMP production and clinical use of these viruses. In some embodiments, this disclosure demonstrates that nucleocytoplasmic transport inhibitors can be used to increase the yield of poxviruses, including oncolytic virus candidates such as vaccinia virus (VACV) and myxoma virus (MYXV), when applied to poxvirus GMP manufacture in immortalized human or primate cells.

Methods of Use

The present disclosure provides a method of increasing poxvirus production yields in transformed human and primate cells, for example, those commonly used for GMP manufacture or viruses, such as oncolytic viruses. In comparison with other viruses that have been put forward as oncolytic virus candidates, poxviruses such as MYXV and VACV present some unique challenges in large-scale manufacture and purification. As some of the largest viruses in nature, poxviruses are visible by light microscopy, and measure 200-400 nanometers (nm) in length as described in Moss, in Fields' virology B. N. Fields, D. M. Knipe, P. M. Howley, D. E. Griffin, Eds. (Lippincott Williams & Wilkins, Philadelphia, 2001) pp. 2849-2883, which is incorporated herein by reference in its entirety. Due to its large size, vaccinia virus cannot be sterilized by filtration and thus any manufacturing process is typically closed. With its entire life cycle occurring within the host cell cytoplasm, the bulk of infectious particles are not released into the cellular medium, but are retained within the infected cell, thus purification requires the lysis of the infected cell and the purification of the viral particles from the cellular debris.

Disclosed herein, in some embodiments, are methods of treating immortalized human cell lines with agents, such as small molecules, that inhibit the nuclear export pathway, for example when added just before the time of virus adsorption. Culturing the cells in the presence of the agents, for example, throughout subsequent infection cycles, can increase the replication and ultimate yields of overall infectious poxvirus. The disclosed method thus provides an elegant way to increase the overall yield of poxviruses, such as myxoma virus (MYXV) and vaccinia virus (VACV), in transformed human and primate cells used for virus GMP manufacture.

The use of the nucleocytoplasmic transport inhibitor increases the replication of poxvirus. In some embodiments, the poxvirus is replicated at a rate that is at least 20%, 30%, 40%, 50%, 60%, 70%, 80%, 90% faster than the replication rate in the absence of the nucleocytoplasmic transport inhibitor. In some embodiments, the poxvirus is replicated at a rate that is at least 1.5 times, 2 times, 2.5 times, 3 times, 3.5 times, 4 times, 5 times, 6 times, 7 times, 8 times, 9 times, or 10 times faster than the replication rate in the absence of the nucleocytoplasmic transport inhibitor.

In some embodiments, the nucleocytoplasmic transport inhibitor increases the replication of poxvirus by at least 30%, 50%, 70%, 90%, 2 fold, 3 fold, 5 fold, 7 fold, 9 fold, 10 fold, 12 fold, or 15 fold after 24 hours post infection. In some embodiments, the nucleocytoplasmic transport inhibitor increases the replication of poxvirus by no more than 5 fold, 10 fold, 12 fold, 15 fold, 20 fold, 30 fold, 50 fold, 70 fold, or 100 fold after 24 hours post infection.

Aspects of the present disclosure concern a method of producing poxviruses at an increased growth rate and/or titer in cells. In some embodiments, the method includes contacting host cells with an effective amount of nucleocytoplasmic transport inhibitor (which may also be referred to as a nuclear export pathway inhibitor). The concentration of inhibitor can be chosen to be below that which would normally cause any cytotoxic or anti-viral effects, but still sufficient to result in an increase in the production of the poxvirus of interest. In some embodiments, an effective amount of a nucleocytoplasmic transport inhibitor is between about 0.000001 μM and about 0.1 μM, such as about between about 0.000001 μM, about 0.00001 μM, about 0.0001, about 0.0005 μM and about 0.05 μM, such as about 0.0005 μM, about 0.001 μM, about 0.0015 μM, about 0.002 μM, about 0.0025 μM, about 0.003 μM, about 0.0035 μM, about 0.004 μM, about 0.0045 μM, about 0.005 μM, about 0.01 μM, about 0.015 μM, about 0.02 μM, about 0.025 μM, about 0.03 μM, about 0.035 μM, about 0.04 μM, about 0.045 μM, and about 0.05 μM. In certain embodiments, the nucleocytoplasmic transport inhibitor includes one or more of Leptomycin A, Leptomycin B, Ratjadone A, B, C and D, Anguinomycin A, Goniothalamin, piperlongumine, plumbagin, curcumin, valtrate, acetoxychavicol acetate, prenylcoumarin osthol, or synthetic nucleocytoplasmic transport inhibitors such as KOS 2464, PKF050-638 (N-azolylacrylate analog), CBS9106, Selinexor, and those found in Mathew and Ghildyal, CRM1 inhibitors for antiviral therapy, Frontiers in Microbiology 2017, Vol 8, article 1171, which is specifically incorporated herein by reference.

In certain embodiments, the poxvirus of interest is genetically modified. For example, the poxvirus of interest can be modified to carry any other gene, such as a therapeutic gene, and/or to delete or disrupt one or more endogenous viral genes. In the case of viruses modified to treat cancer, the gene would typically be selected to enhance the anticancer effect of the treatment. Such a gene may be a gene that is involved in triggering apoptosis, or is involved in targeting the infected cell for immune destruction, such as a gene that repairs a lack of response to interferon, or that results in the expression of a cell surface marker that stimulates an antibody response, such as a bacterial cell surface antigen. The virus may also be modified to express genes involved in shutting off the neoplastic or cancer cell's proliferation and growth, thereby preventing the cells from dividing. As well, the virus may be modified to include therapeutic genes, such as genes involved in the synthesis of chemotherapeutic agents, or it may be modified to have increased replication levels in cells of the particular species from which the cells to be inhibited or killed are derived, for example, human cells.

Oncolytic viruses are mammalian viruses that are designed and/or selected for their ability to selectively infect and kill transformed cancer cells, and by their ability to activate the host immune system against not only the virus, but also tumor antigens (Lichty B D, Breitbach C J, Stojdl D F, Bell J C. 2014. *Going viral with cancer immunotherapy*. Nature Reviews Cancer 14:559-567). Myxoma virus (MYXV) is potentially well suited as a therapeutic virus against solid cancers, such as osteosarcoma, because of its unique biology. MYXV is a member of the family poxviridae and genus leporipoxvirus (Chan W M, Rahman M M, McFadden G. 2013. Oncolytic Myxoma virus: the path to clinic. Vaccine 31:4252-4258; Chan W M, McFadden G. 2014. Oncolytic poxviruses. Annual review of virology 1:191-214). Thus, in certain embodiments, a poxvirus of interest is an oncolytic virus candidate. In certain embodiments, the poxvirus of interest is a Leporipoxvirus, such as a myxoma virus. In certain embodiments, the poxvirus of interest is an Orthopoxvirus, such as a vaccinia virus, including different strains of vaccinia virus such as Lister, Wyeth, Western Reserve (WR), Modified Vaccinia virus Ankara (MVA), and LC16m series; and Raccoonpox virus (RCNV). In certain embodiments, the poxvirus of interest is a Yatapoxvirus, such as a Tanapoxvirus (TPV) or Yaba-like disease virus (YLDV). In certain embodiments, the poxvirus of interest is a capripox virus, such as Orf virus.

In certain embodiments, host cells are immortalized human or primate cells. In certain embodiments, host cells are a cell line used in good manufacturing practices (GMP) for manufacture of a virus. In a specific embodiment, host cells are Human A549 cells, HeLa cells, 239 cells, or primate Vero cells.

EXAMPLES

Example 1: Nucleocytoplasmic Transport Inhibitors

The nuclear pore complex (NPC) mediates all movement across the cell nuclear envelope. Proteins to be imported into the cell nucleus contain sequences termed nuclear localization sequences (NLS), and proteins to be exported from the nucleus contain nuclear export sequences (NES). These signals are recognized by soluble factors that work with the Ran GTPase cycle to coordinate export or import from nucleus (Pemberton, L. F. and B. M. Paschal, *Mechanisms of receptor-mediated nuclear import and nuclear export*. Traffic, 2005. 6(3): p. 187-98). For export, CRM1/exportin-1 (chromosome region maintenance 1) protein directly binds proteins that contain a leucine rich NES. Both natural products and small chemical molecules have been identified that exert inhibitory effects on nuclear export processes (nucleocytoplasmic transport inhibitors). Leptomycin B (LMB) is a nucleocytoplasmic transport inhibitor that functions by directly targeting CRM1. LMB is a polyketide isolated from *Streptomyces* (Mutka, S. C., et al., *Identification of nuclear export inhibitors with potent anticancer activity in vivo*. Cancer Res, 2009. 69(2): p. 510-7; Turner, J. G., J. Dawson, and D. M. Sullivan, *Nuclear export of proteins and drug resistance in cancer*. Biochem Pharmacol, 2012. 83(8): p. 1021-32). LMB covalently binds to the Cys528 in the CRM1 NES groove. This irreversible binding of LMB with CRM1 subsequently inhibits CRM1 interaction with the nuclear export signal of targeted export proteins (Kudo, N., et al., *Leptomycin B inhibition of signal-* mediated nuclear export by direct binding to CRM1. Exp Cell Res, 1998. 242(2): p. 540-7). LMB inhibits the G1 and G2 phases of the cell cycle and other cellular functions. Due to this irreversible interaction, LMB can be toxic to the cells when dosed at high concentrations. LMB also has been tested as an anti-viral drug as it blocks replication of certain viruses that rely on nuclear export. Like LMB, Leptomycin A (LMA) is isolated from *Streptomyces* and inhibits nuclear export by binding to CRM1. Ratjadone analogs isolated from myxobacterium *Sorangium cellulosum*, have similar structure to LMB and use the same molecular mechanism to inhibit CRM1 (Koster, M., et al., *Ratjadones inhibit nuclear export by blocking CRM1/exportin* 1. Exp Cell Res, 2003. 286(2): p. 321-31). LMB arrests cells at the G1 phase at very low concentration (50 pg/ml in HeLa cells). Another natural compound, Anguinomycin isolated from *Streptomyces* species, has been reported to shutdown CRM1-mediated nuclear protein export at concentrations above 10 nM (Dickmanns, A., T. Monecke, and R. Ficner, *Structural Basis of Targeting the Exportin CRM1 in Cancer*. Cells, 2015. 4(3): p. 538-68). It also interacts with CRM1 in a similar mechanism to LMB. Apart from the natural inhibitors of nuclear export, there are also synthetic CRM1 inhibitors which can have less toxicity and can be used for the same purpose.

Figure 1A:
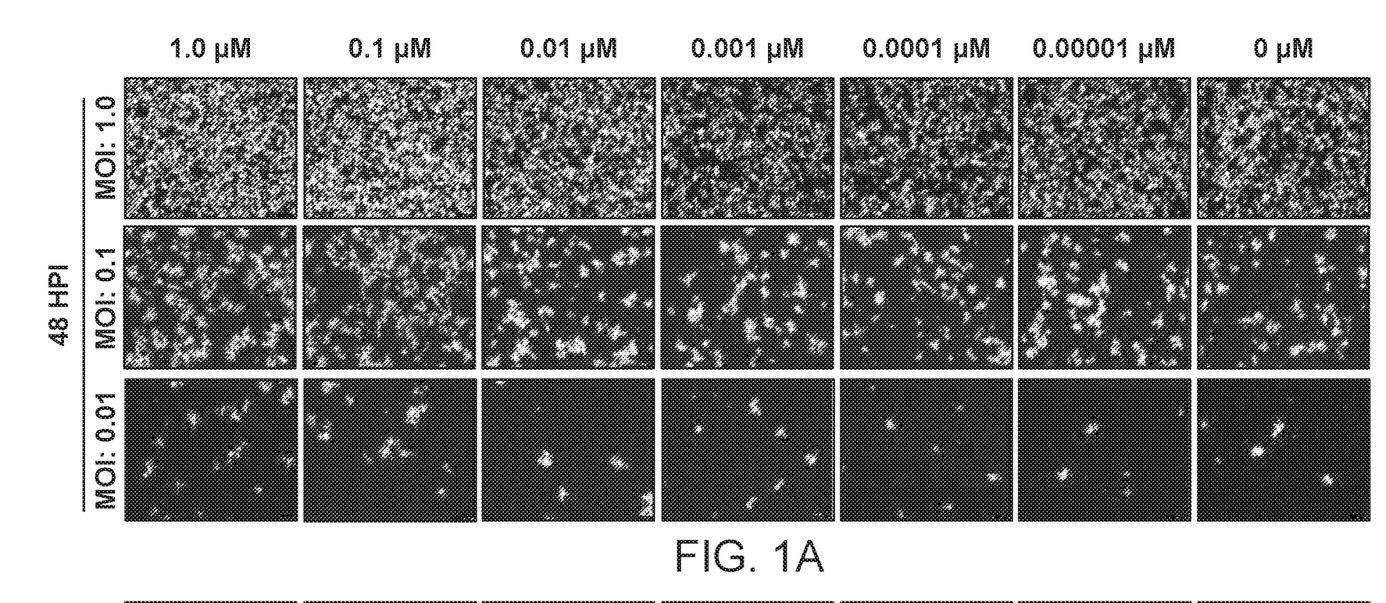
FIGS. 1A and 1B are a set of digital images showing that treatment of human A549 cells with nucleocytoplasmic transport inhibitor Leptomycin A enhanced myxoma virus (MYXV) replication, as indicated by reporter gene expression (GFP fluorescence). A549 cells were pre-treated with different concentrations of Leptomycin A for 1 h and infected with vMyx-GFP at an MOI of 1.0, 0.1 or 0.01 in the presence of the inhibitor. Fluorescence images were taken at 48 h (FIG. 1A) and 72 h (FIG. 1B) post infection using a fluorescence microscope.
Figure 1B:
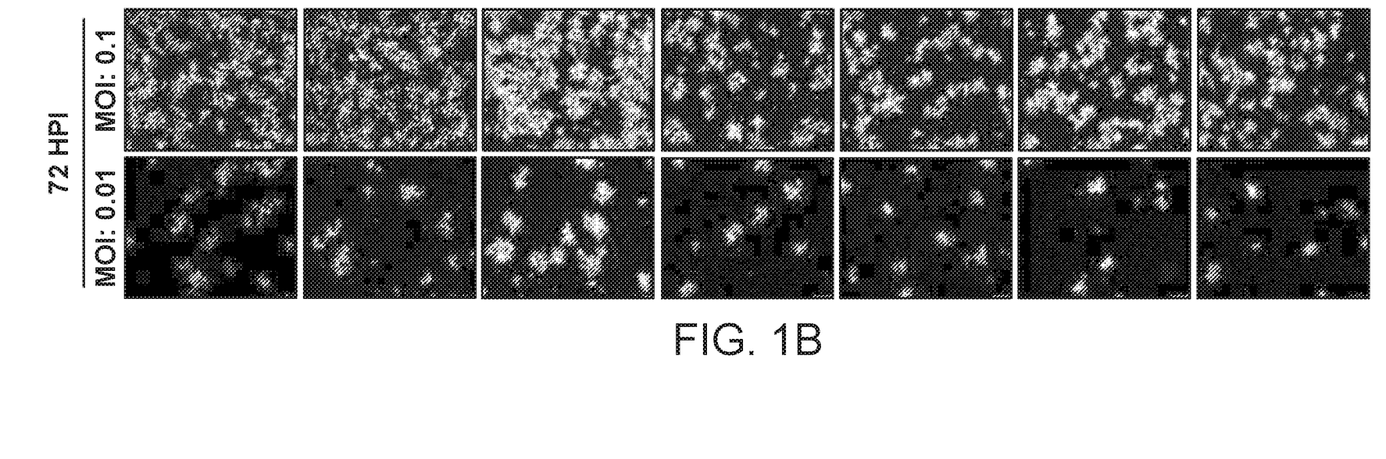
Figure 2A:
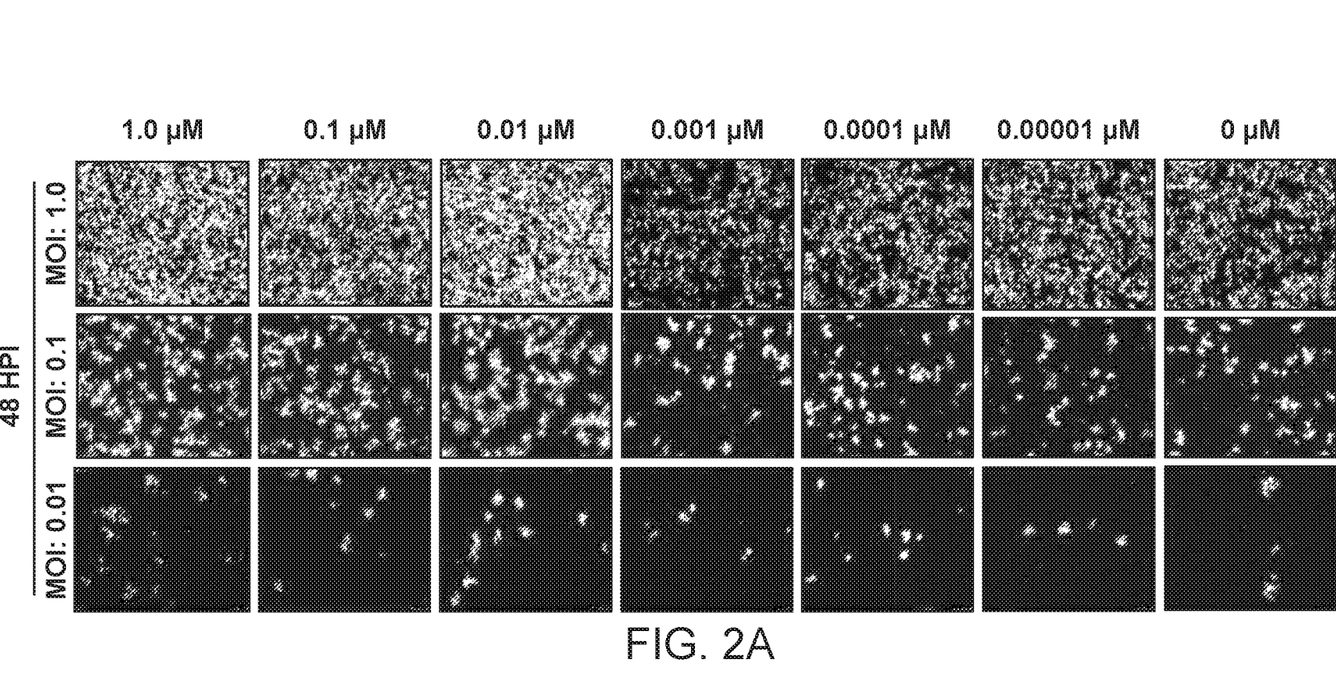
FIGS. 2A and 2B are a set of digital images showing that treatment of human A549 cells with nucleocytoplasmic transport inhibitor Leptomycin B enhanced MYXV replication, as indicated by reporter gene expression (GFP fluorescence). A549 cells were pre-treated with different concentrations of Leptomycin B for 1 h and infected with vMyx-GFP at an MOI of 1.0, 0.1 or 0.01 in the presence of the inhibitor. Fluorescence images were taken at 48 h (FIG. 2A) and 72 h (FIG. 2B) post infection using a fluorescence microscope.
Figure 2B:
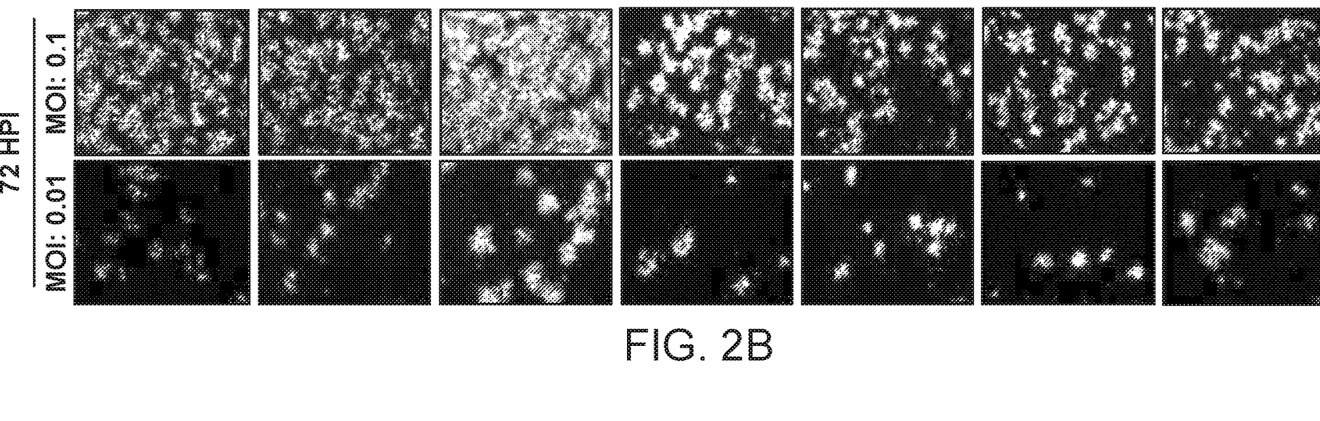
Figure 3A:
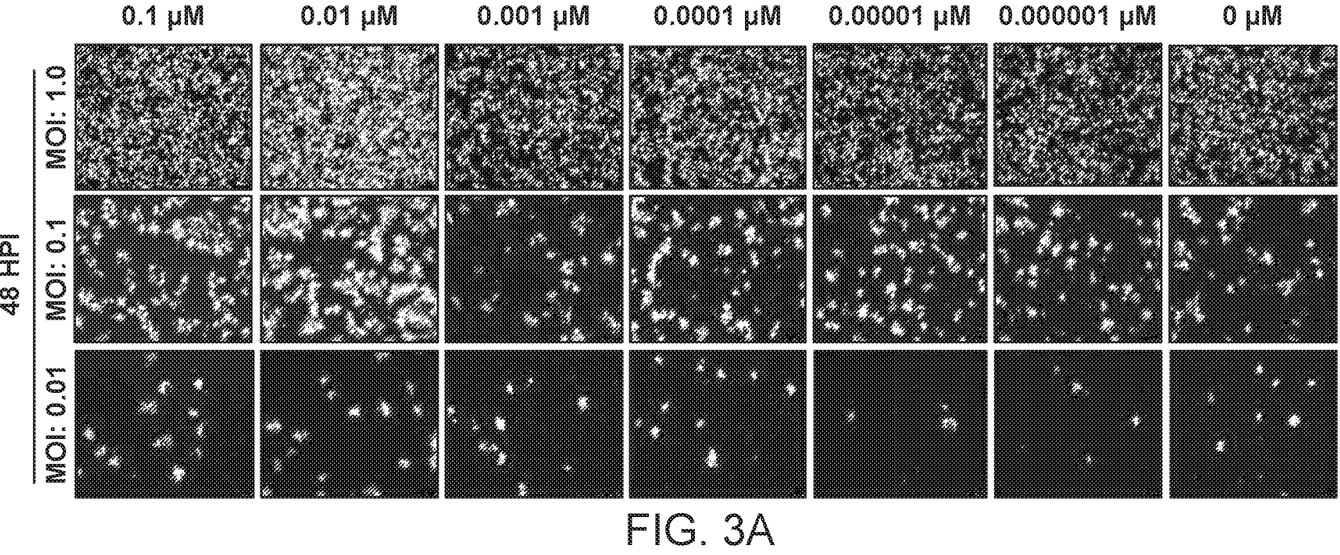
FIGS. 3A and 3B are a set of digital images showing that treatment of human A549 cells with nucleocytoplasmic transport inhibitor Ratjadone A enhanced MYXV replication, as indicated by reporter gene expression (GFP fluorescence). A549 cells were pre-treated with different concentrations of Ratjadone A for 1 h and infected with vMyx-GFP at an MOI of 1.0, 0.1 or 0.01 in the presence of the inhibitor. Fluorescence images were taken at 48 h (FIG. 3A) and 72 h (FIG. 3B) post infection using a fluorescence microscope.
Figure 3B:
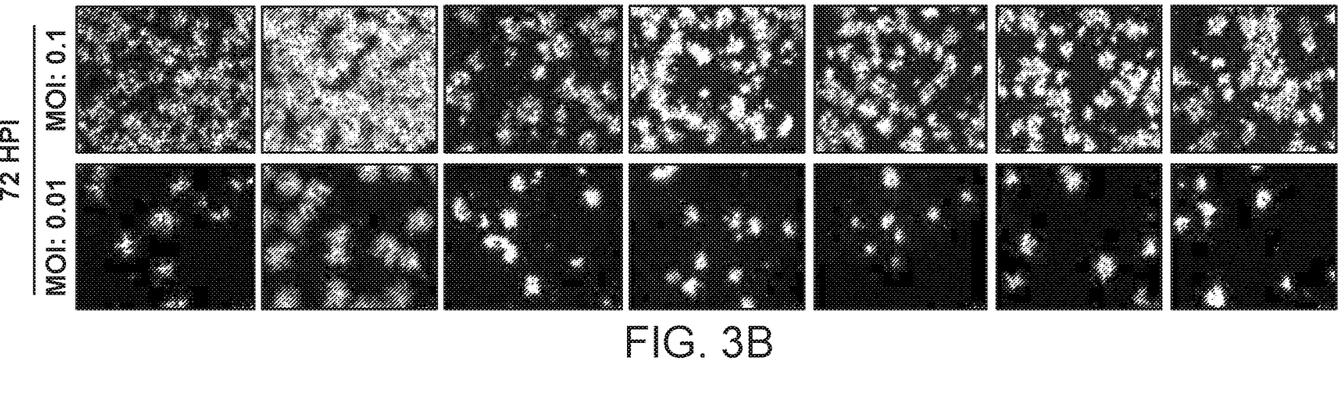
Figure 4A:
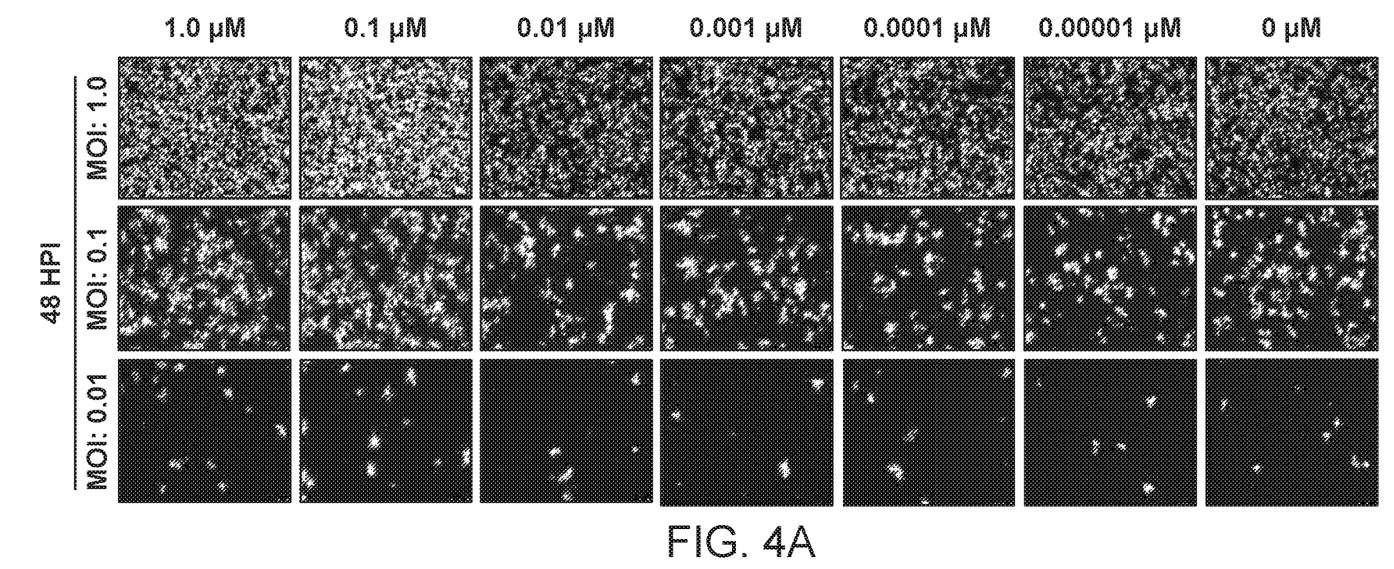
FIGS. 4A and 4B are a set of digital images showing that treatment of human A549 cells with nucleocytoplasmic transport inhibitor Anguinomycin A enhanced MYXV replication, as indicated by reporter gene expression (GFP fluorescence). A549 cells were pre-treated with different concentrations of Anguinomycin A for 1 h and infected with vMyx-GFP at an MOI of 1.0, 0.1 or 0.01 in the presence of the inhibitor. Fluorescence images were taken at 48 h (FIG. 4A) and 72 h (FIG. 4B) post infection using a fluorescence microscope.
Figure 4B:
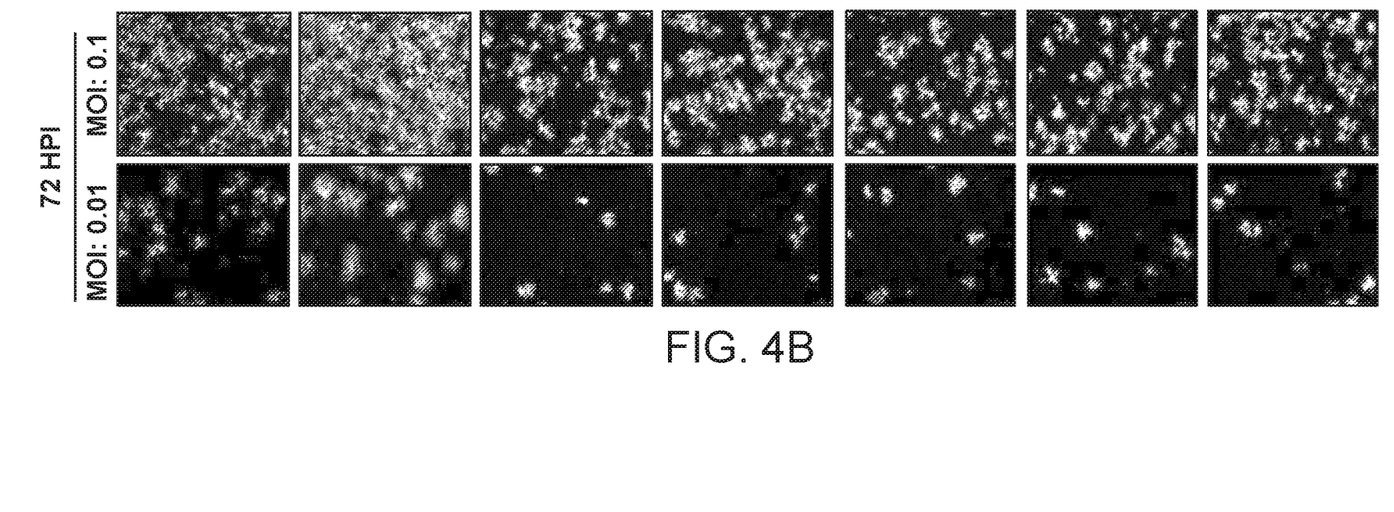

Example 2: Nucleocytoplasmic Transport Inhibitors Enhance MYXV Replication as Indicated by Reporter Gene Expression in Human Cells Unlike rabbit cells, in primary human cells the infection and replication of Myxoma virus (MYXV) is often restricted at multiple stages of replication cycle by the intracellular anti-viral signaling pathways. Many human cancer cells are permissive to MYXV because these anti-viral pathways are frequently compromised or absent in the cancer cells. Like other poxviruses, it is not clearly documented what roles nuclear proteins have during MYXV replication in primary or transformed human cells. However, many nuclear proteins that shuttle between the two cellular compartments may either inhibit or upregulate MYXV replication. To test the effect of nuclear proteins in MYXV replication, Nucleocytoplasmic transport inhibitors were used to inhibit the nuclear export of cellular proteins during MYXV replication. For this study, Leptomycin A (FIGS. 1A and 1B), Leptomycin B (FIGS. 2A and 2B), Ratjadone A (FIGS. 3A and 3B) or Anguinomycin A (FIGS. 4A and 4B) were tested as representative nucleocytoplasmic transport inhibitors. Human A549 cells were mock treated or pre-treated with the inhibitors at different concentration for 1 hour (h) and then infected with MYXV expressing a GFP reporter gene (vMyx-GFP) at different multiplicities of infection (MOI). The cells were observed under fluorescence microscope to monitor GFP expression as an indicator for the progression of viral replication. At certain concentrations of all the tested inhibitors, we observed enhanced GFP expression, which also increased the MYXV foci size when infected with virus at an MOI of less than 0.1. Published reports suggest these virus replication-enhancing concentrations of the inhibitors are associated with minimal toxicity to the cells (Kalesse, M., et al., *The chemistry and biology of ratjadone*. Chembiochem, 2001. 2(9): p. 709-14).

Figure 5A:
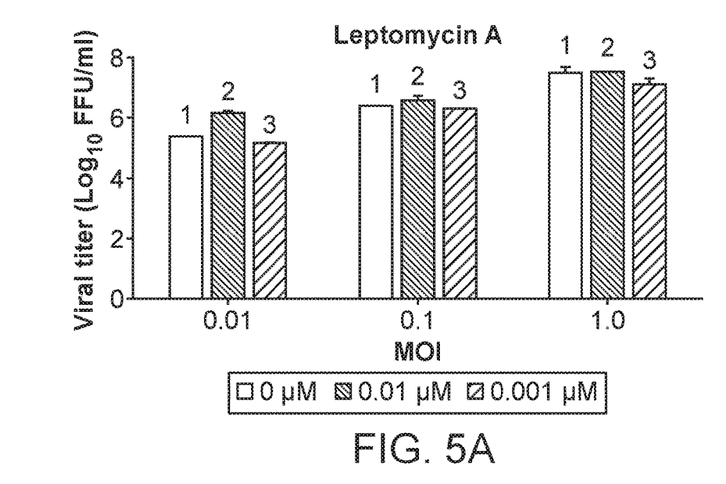
Figure 5B:
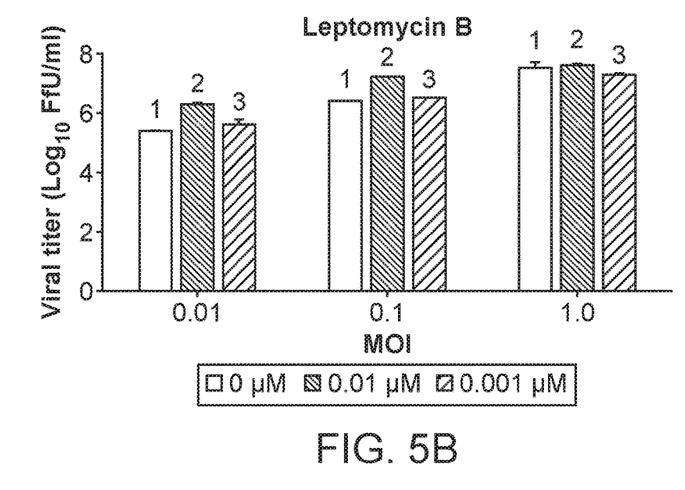
Figure 5C:
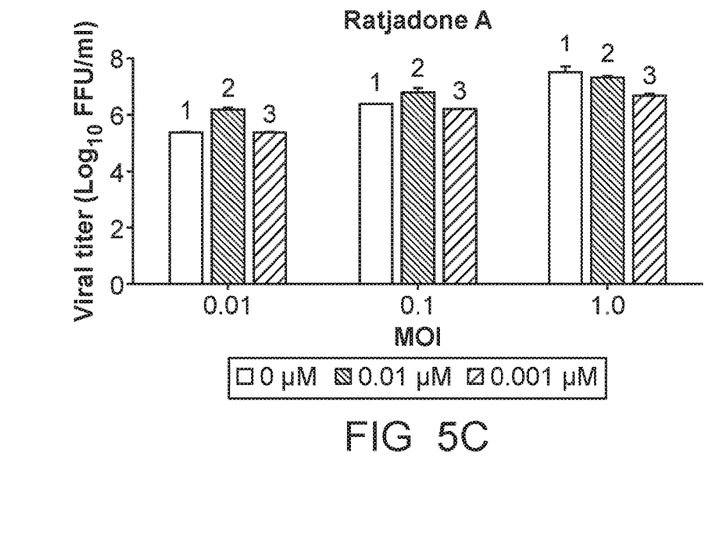
Figure 5D:
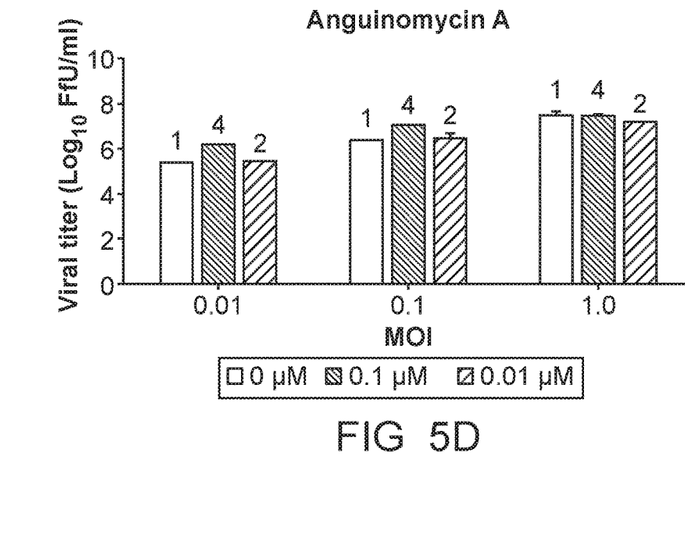
Figure 6A:
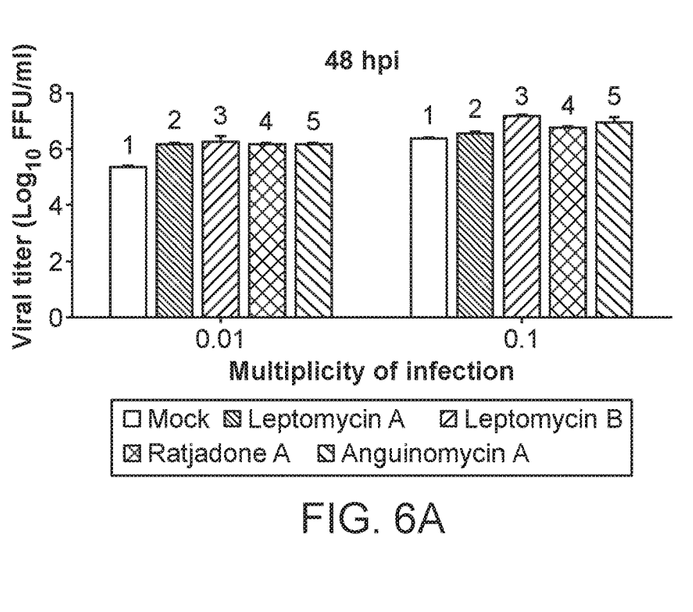
Figure 6B:
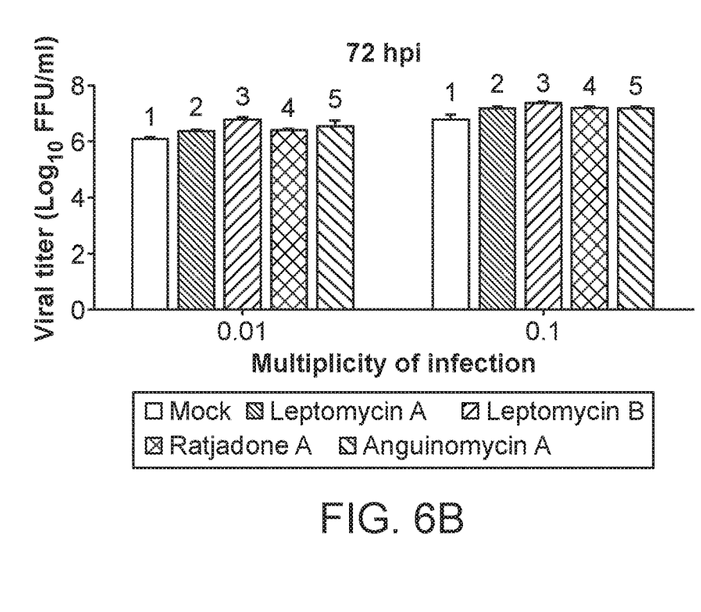

Example 3: Nucleocytoplasmic Transport Inhibitors Enhance MYXV Progeny Virus Production To quantitatively assess whether the observed effect of nucleocytoplasmic transport inhibitors on viral reporter gene expression (GFP) can be reflected in progeny virus formation, quantitative virus titration assays were performed. Human A549 cells were mock treated or pre-treated with the inhibitors at two different doses. 1 hour (h) after adding the inhibitors, the cells were infected with vMyx-GFP at an MOI of 1.0, 0.1 and 0.01 for an additional 1 hour. The unadsorbed virus was removed, and cells were incubated with media containing the same concentrations of the inhibitors. The cells were harvested at 48 and 72 hours post infection (hpi) and the formation of progeny virions were titrated in permissive rabbit RK13 cells. At 48 hpi, all the tested nucleocytoplasmic inhibitors significantly enhanced progeny MYXV formation between 5 to 10 fold when infected with low MOI (0.1 or 0.01) and treated with the drug concentration that maximally enhanced MYXV reporter gene expression (10 nM in FIGS. 5A-5C, 100 nM in FIG. 5D). The lower tested concentration (1 nM in FIG. 5A-5C, 10 nM in FIG. 5D), which showed no effect on reporter gene expression, had a marginal effect on progeny virus formation. The concentrations of inhibitors are indicated by the numbers above the bars of the FIG. 5A-FIG. 5D graphs. 1 denotes no inhibitor, 2 denotes 0.01 µM (10 nM) of inhibitor. 3 denotes 0.001 µM (1 nM) of inhibitor, 4 denotes 0.1 µM (100 nM) of inhibitor. Enhanced progeny virus formation was not observed when cells were infected with an MOI of 1.0 or above. These observations suggest that in the conditions of this assay, a certain concentration of the nucleocytoplasmic transport inhibitors enhanced MYXV replication when infected at a low MOI i.e. 0.1 or lower. Leptomycin B exhibited the highest progeny virus production enhancement compared to the other tested drugs (FIGS. 6A and 6B). The treatments in FIG. 6A and FIG. 6B are indicated by the numbers above the bars of the graph; 1 indicates mock treatment, 2 indicates Leptomycin A, 3 indicates Leptomycin B, 4 indicates Ratjadone A, and 5 indicates Anguinomycin A.

Figure 7A:
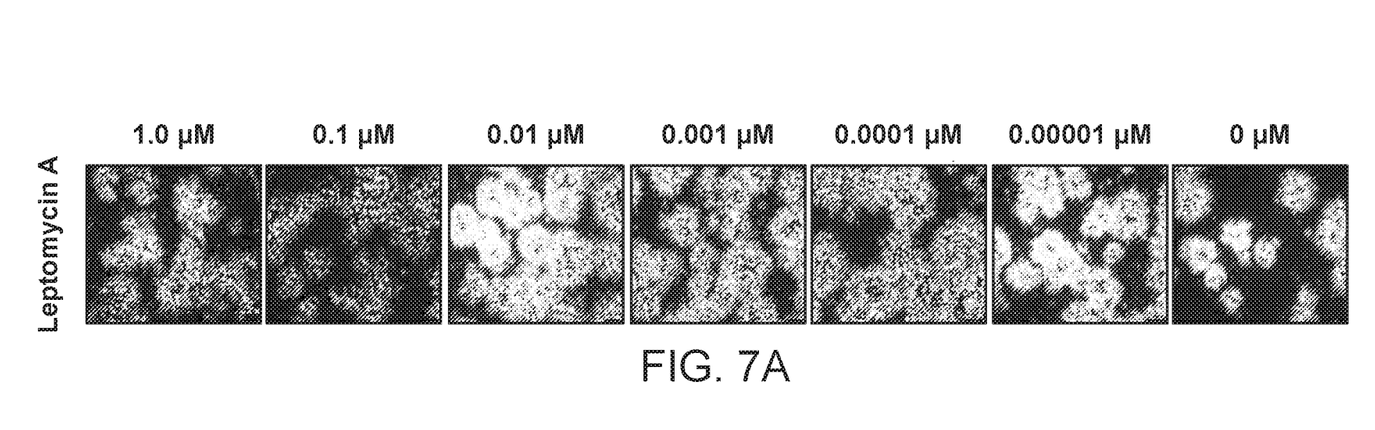
FIGS. 7A and 7B are a set of digital images showing the treatment of human A549 cells with nucleocytoplasmic transport inhibitors enhanced VACV replication, as indicated by reporter gene expression (GFP fluorescence). A549 cells were pre-treated with different concentrations of Leptomycin A (FIG. 7A) or Leptomycin B (Figure. 7B) for 1 h and infected with VACV-GFP at an MOI of 0.03 in the presence of the inhibitors. Fluorescence images were taken at 48 h post infection using a fluorescence microscope.
Figure 7B:
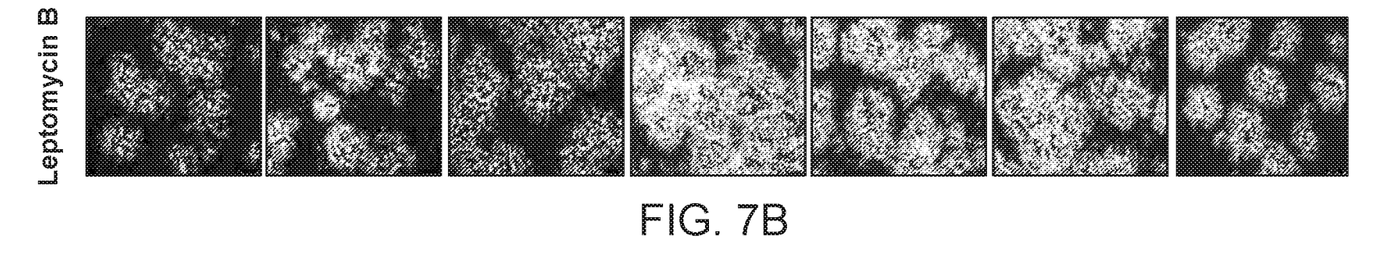
Figure 8A:
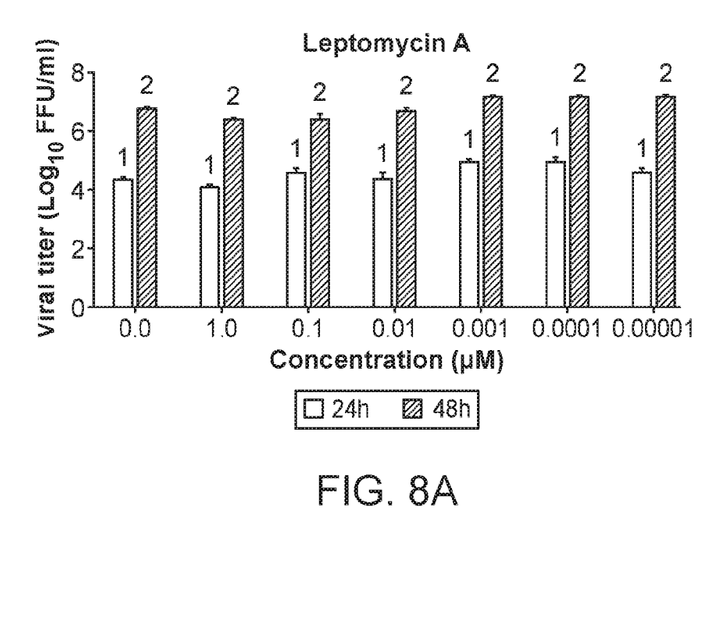
FIGS. 8A and 8B are a set of bar graphs showing that nucleocytoplasmic transport inhibitors enhanced VACV replication in human A549 cells, resulting in higher levels of progeny virus. A549 cells were pre-treated with nucleocytoplasmic transport inhibitors Leptomycin A (FIG. 8A) or Leptomycin B (FIG. 8B) for 1 h. The cells were then infected with VACV-GFP at an MOI of 0.03 for 1 h. After 1 h the un-adsorbed viruses were removed, the cells washed, and incubated with media in the presence of the respective inhibitors. The infected cells were harvested after 24 h (indicated by "1" above the graph bar) or 48 h (indicated by "2" above the graph bar) post infection and virus titers were determined following serial dilutions onto RK13 cells.
Figure 8B:
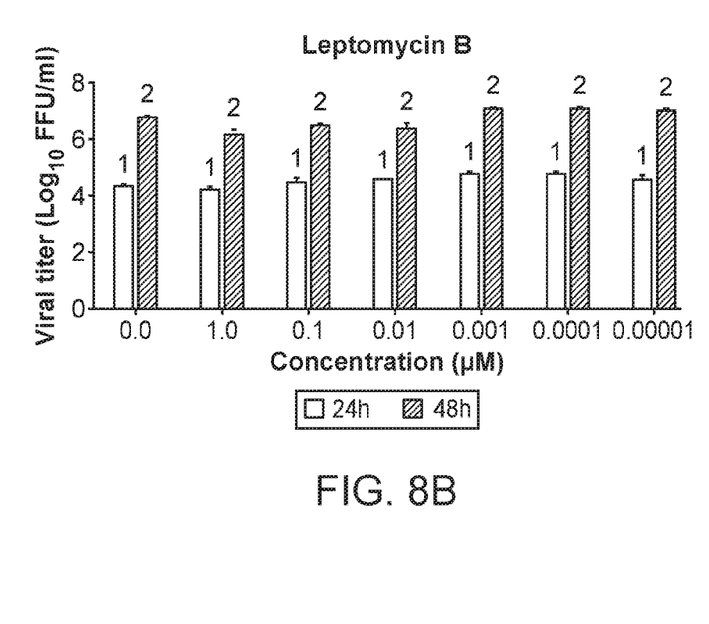

Example 4: Nucleocytoplasmic Transport Inhibitors Enhance VACV Reporter Gene Expression and Progeny Virus Production To test whether the observed effects of nucleocytoplasmic transport inhibitors on MYXV replication is true for other poxviruses, vaccinia virus (VACV) was tested as representative member of orthopoxviruses. For this study, Leptomycin A and Leptomycin B were tested to monitor the influence of these drugs on VACV replication in the same test human cells. Human A549 cells were mock treated or pre-treated with the inhibitors at different concentrations for 1 hour and then infected with VACV expressing GFP (VACV-GFP) with an MOI of 0.03. The cells were observed under fluorescence microscope to monitor the expression of GFP as a marker of the progression of virus replication (FIGS. 7A and 7B). At this time point, both the inhibitors enhanced GFP expression at the concentration of 0.01 µM (10 nM). Enhanced GFP expression was also observed at the lowest dilution of the inhibitors (0.00001 µM or 0.01 nM). It was then tested if the observed effect of nucleocytoplasmic transport inhibitors on virus reporter gene expression can be reflected in enhanced VACV progeny virus formation by performing virus replication assays. Human A549 cells were mock treated or pre-treated with the inhibitors at different concentrations. After 1 h of adding the inhibitors, the cells were infected with VACV-GFP at an MOI of 0.03 for an additional 1 hour. The un-adsorbed virus was removed, and cells were incubated with media containing the same concentration of the nucleocytoplasmic transport inhibitors. The cells were harvested at 24 and 48 hours post-infection (hpi) and the progeny virions were titrated in RK13 cells. Both Leptomycin A and B significantly enhanced progeny VACV formation between 5 to 10 fold at the MOI tested (FIGS. 8A and 8B). The numbers atop the bars of the graphs in FIG. 8A and FIG. 8B indicate the time points: 1 indicates 24 h, while 2 indicates 48 h. The enhanced viral titer also correlated with the enhanced viral reporter gene expression. These observations demonstrate that nucleocytoplasmic transport inhibitors can enhance replication of orthopoxvirus, like VACV, leporipoxviruses such as MYXV, and other poxviruses.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims. We therefore claim as our invention all that comes within the scope and spirit of these claims.

We claim:

1. A method of producing a poxvirus at an increased growth rate or titer, the method comprising:
   contacting a host cell with a nucleocytoplasmic transport inhibitor at a concentration of at least 0.01 µM; wherein the host cell is a transformed cell;
   contacting the host cell with a poxvirus, wherein the host cell is contacted with the poxvirus at a multiplicity of infection (MOI) less than one; and
   culturing the host cell to produce progeny of the poxvirus at an increased growth rate compared to the growth rate in identical conditions lacking the nucleocytoplasmic transport inhibitor or an at least 3-fold increase in titer compared to that produced in identical conditions lacking the nucleocytoplasmic transport inhibitor,
   wherein the nucleocytoplasmic transport inhibitor is one or more selected from the group consisting of: Leptomycin A, Leptomycin B, Ratjadone A, Ratjadone B, Ratjadone C, Ratjadone D, and Anguinomycin A; and
   wherein the poxvirus is myxoma virus.

2. The method of claim 1, further comprising harvesting the progeny of the poxvirus.

3. The method of claim 1, wherein the host cell is contacted with the nucleocytoplasmic transport inhibitor prior to contacting the host cell with the poxvirus.

4. The method of claim 1, wherein the host cell is contacted with the nucleocytoplasmic transport inhibitor after contacting the host cell with the poxvirus.

5. The method of claim 1, wherein the host cell is contacted with the nucleocytoplasmic transport inhibitor and the poxvirus at the same time.

6. The method of claim 1, wherein the poxvirus is genetically modified.

7. The method of claim 1, wherein the culturing is conducted under good manufacturing practices (GMP) for manufacture of the poxvirus.

8. The method of claim 1, wherein the host cell is contacted with the poxvirus at a multiplicity of infection (MOI) of between about 0.01 and about 0.1.

9. The method of claim 1, wherein the increase in viral titer is evaluated 24 hours or 48 hours after contacting the host cell with the poxvirus.

10. A method for replicating a leporipoxvirus, the method comprising:
    exposing a host cell to a nucleocytoplasmic transport inhibitor at a concentration of at least 0.01 µM; wherein the host cell is a transformed cell;
    infecting the host cell with a leporipoxvirus at a multiplicity of infection (MOI) less than 1, thereby generating an infected host cell; and
    incubating the infected host cell in a culture medium under conditions that allow for replication of the leporipoxvirus,
    wherein the rate of replication is greater than the rate of replication in identical conditions lacking the nucleocytoplasmic transport inhibitor or an at least 3-fold increase in titer compared to that produced in identical conditions lacking the nucleocytoplasmic transport inhibitor
    wherein the nucleocytoplasmic transport inhibitor is one or more selected from the group consisting of: Leptomycin A, Leptomycin B, Ratjadone A, Ratjadone B, Ratjadone C, Ratjadone D, and Anguinomycin A; and
    wherein the leporipoxvirus is a myxoma virus.

11. The method of claim 1, wherein the host cell is A549 cell.

12. The method of claim 10, wherein the host cell is A549 cell.

* * * * *